United States Patent [19]

Stewart

[11] Patent Number: 5,229,833
[45] Date of Patent: Jul. 20, 1993

[54] OPTICAL SENSOR

[75] Inventor: William J. Stewart, Blakesley, England

[73] Assignee: GEC-Marconi Limited, Stanmore, England

[21] Appl. No.: 765,891

[22] Filed: Sep. 26, 1991

[30] Foreign Application Priority Data

Sep. 26, 1990 [GB] United Kingdom ............. 9020965

[51] Int. Cl.$^5$ .............................................. G01N 21/17
[52] U.S. Cl. .................................. 356/364; 356/128; 356/352
[58] Field of Search ............ 356/364, 369, 370, 128, 356/352

[56] References Cited

U.S. PATENT DOCUMENTS 5,076,696 12/1991 Cohn et al. ................... 356/369

FOREIGN PATENT DOCUMENTS

| 0257955 | 8/1987 | European Pat. Off. |
| 0305109 | 8/1988 | European Pat. Off. |
| 2156970 | 10/1985 | United Kingdom |
| 2174802A | 11/1986 | United Kingdom |
| 2197065A | 5/1988 | United Kingdom |
| 2197068A | 5/1988 | United Kingdom |
| 2227089A | 7/1990 | United Kingdom |
| WO90/08318 | 7/1990 | World Int. Prop. O. |
| WO92/04617 | 3/1992 | World Int. Prop. O. |

OTHER PUBLICATIONS

Murray, Thomas P. "Automatic Optical Thickness Gauge for Thin Film Measurements", *The Review of Scientific Instruments.* vol. 33, No. 2 (Feb. 1962). pp. 172-176.

*Primary Examiner*—Richard A. Rosenberger
*Attorney, Agent, or Firm*—Jacobson, Price, Holman & Stern

[57] ABSTRACT

An optical sensor includes a resonant mirror device 1, and a prism 2 disposed adjacent the device for coupling a beam of light into the device 1. The device 1 and the prism 2 are mounted on a rotatable platform. A beam of light is produced by He-Ne laser 3 and is linearly polarized with equal TE and TM components by a polarizer 4 arranged at 45° to TE and TM axis. A lens 6 is arranged in the path of the linearly polarized beam of light for focussing the beam of light onto the device thereby providing simultaneously a range of angles of incidence at which the beam of light can be coupled into said device. The platform on which the device 1 and the prism 2 are mounted, is rotated to a position, at which the angle of incidence of beam of light coupled into the device is such that a resonance is excited in said device for at least one of said components. The beam of light reflected from the device is passed through an analyser 11 arranged at 90° to the polarizer 4. On resonance of one or both components, one component is phase shifted to the other between 0 and 2 radians. The beam in this case will be elliptically polarized light and at least a component of light will be passed by the analyser 11 and will be projected as a bright band on a viewing plane. When the phase shift is radian, the beam is linearly polarized, but in the plane of the transmission axis of the analyser and so all the light is transmitted by the analyser.

8 Claims, 3 Drawing Sheets

OPTICAL SENSOR

The invention relates to an optical sensor and a method of testing a chemical sample.

There is need for immunological test devices for body fluids which satisfy the following criteria:
no sample preparation required,
small volume of fluid required (pinprick samples),
simultaneous testing of a number of analytes (3),
cheap, disposable testing elements,
short readout time,
desk top instrumentation.

Analysis systems satisfying these criteria will be of particular use in doctors surgeries, allowing them to carry out on the spot analyses. This has obvious advantages for the rapid diagnosis and treatment of disease, as well as being convenient for the patient. A number of technologies are currently under investigation for this application, including acoustic, amperometric, electrochemical and optical devices, in combination with biologial sensing layers consisting of monoclonal antibodies.

Immunosensing utilizes the method used by the body's immune system to identify foreign material. The body generates protein molecules, known as antibodies, which are capable of binding to the foreign material, the antigen, in a highly specific manner so aiding its identification and destruction. Most chemicals with molecular weights above 250 can induce the production of antibodies, with larger structures, such as bacteria and parasites, giving rise to multiple antibodies, each with a different binding site on the structure. Antibodies can therefore be used as a very powerful tool for the identification and detection of specific antigens.

A major use of these antibodies is in the clinical assay of body fluids for the detection of disease and abnormality, and in the monitoring of therapeutic drug treatment. The difficulty is to detect the antibody-antigen binding reaction. The antibody molecules are typically only 50–100 A in size and so are very difficult to detect by direct means. Most assays are carried out by attaching a label to the antibody molecule. Typical labels are radioactive or fluorescent molecules, or enzymes. Techniques using these allow for the accurate assays to be carried out, typically in the concentration ranges 10-6-10-15 molar. However they require reasonably large volumes of sample and involve complex procedures which need to be carried out by skilled personnel in a laboratory environment. To simplify these tests would represent a breakthrough in the use of clinical assay.

Optical techniques have been utilized for some time in the field of biosensors, monitoring reactions by measuring changes in absorption, fluorescence, scatter and refractive index, often remotely by the use of optical fibres. In particular, for immunosensing, great interest has been shown in evanescent optical sensors. These utilize the ability to immobilize antibodies in monolayers on a variety of substrates. The antibodies are immobilized onto the surface of a device so that the evanescent field of the light penetrates the antibody layer. Suitable devices include prisms, waveguides, gratings and fibres. Any binding reactions occuring at the antibody layer affects the evanescent field and hence the optical properties of the device. Using the evanescent wave as the sensing element has a number of advantges:

a) the light path is separated from the "wet" biochemistry,
b) the light probes only a surface layer, not seeing the bulk of the sample,
c) the volume of liquid required is only that which the evanescent field occupies—a few nanoliters.

In this way, the bulk of the sample does not interfere with the light either on its path to and from the sensing region or at the antibody sensing layer, so removing the requirement to separate out, for example, the cells in a blood sample. The small volume means that pinprick samples may be used, so reducing the discomfort caused to the patient, particularly where repeated measurements are to be made.

The binding reaction has been monitored using evanescent techniques which detect the absorption or fluorescence of the antibody molecules, either natural or via a label. More recently binding reactions have been sensed by measuring their effect on the phase of light passing through the bound layers, a consequence of changes in their thickneses and refractive indices. These include surface plasmon resonance sensors and waveguide devices, as well as the resonant mirror device.

Both the surface plasmon resonance (SPR) sensor and the resonant mirror sensor utilize resonance effects in thin films, plasmon resonance of the electrons in a metal (usually silver) film in SPR and optical resonance in a dielectric film in the resonant mirror. Light is coupled into the device and excites resonance at a particular incident angle. In the SPR device, as the resonating electrons radiate energy, light is absorbed by the metal film at resonance and the light reflected from the device is heavily attenuated. By monitoring the intensity of the reflected light as the incident angle is scanned, the position of the resonance is measured.

In the resonant mirror device, there is little attenuation of the light on resonance. However, the phase of the reflected light undergoes a shift of $\pi$ radians, which may be measured using various interferometric techniques, so allowing a measure of resonance position.

In both devices the occurrence of a binding reaction within the evanescent region of the resonant field introduces an additional phase change. As a result, the angle at which resonance occurs is changed and this can be measured as a means of detecting the binding reaction.

These measurements may be made at a wide range of wavelengths (depending on device construction) and be used with any antibody-antigen reaction, without the use of labels. The devices are simple in construction and use and so lend themselves to use as cheap disposable sensors. However, it is believed that the resonant mirror device has a significant advantage over the SPR device. As the resonant structure in the resonant mirror is very low loss the resonance width is greatly reduced (in current devices the width is as low as 3 minutes of arc compared with typical SPR values of 1–1.5 degrees). This allows for much finer resolution of the angular shifts in resonance occuring on binding. When combined with the difference in the angle shift observed, we are left with an achieved increase in sensitivity of 10× that of SPR devices and optimization should enable increase into the region of 100×. In addition, as disclosed in the present invention, the resonant mirror possesses two distinct resonances, one for light polarized in the incident plane and one for light perpendicular to the plane. This allows the refractive index and thickness of the bound layer to be measured. SPR may only be excited by light polarized in the incident plane, reducing the amount of information available and preventing these measurements being made.

Resonant mirror devices used in the present invention may be made from a variety of dielectric materials, using a variety of techniques. The devices can be fabricated by vacuum deposition of standard optical coating materials onto polished glass substrates, and consist of a low refractive index layer (e.g. magnesium fluoride or silica) covered by a thin high index layer (e.g. zirconia or titania). The polished glass substrates are then index matched to glass prisms to allow the coupling of light into the substrate. The devices are 10 mm×12 mm, so that the device may be illuminated with a wedge shaped beam allowing simultaneous monitoring of a number of areas across the device, each of which may be coated with a different antibody. This will allow multiple tests to be carried out on the sample, as required. For the disposable device it is preferred that the coupling element be part of the substrate. Substrates may be glass or polymer, using either prismatic shapes or grating structures to enable coupling. The dielectrc layers may be inorganic or polymer, deposited by vacuum, sol-gel or solvent deposition technique, depending upon the nature of the substrate.

When light is totally internally reflected from a boundary, it undergoes a phase change. The size of the phase change depends upon the refractive indices of the bounding materials, the wavelength of the light and the angle of incidence. Any changes at the boundary, such as antibody-antigen binding reactions, will alter the phase change. However for a simple high/low index boundary, the phase change is very slight and so the device is not very sensitive. In order to increase sensitivity, the resonant mirror device incorporates a resonant structure at the boundary, consisting of a high/low index pair of dielectric layers.

The layer pair acts rather like a Fabry-Perot cavity. One "mirror" of the cavity consists of the low index layer bounded by the two high index materials. Some of the light which is reflected from the lower boundary "tunnels", via the evanescent field, into the high index layer, a process known as frustrated total internal reflection. This layer therefore acts as a partially transmitting mirror, the degree of transmission being determined by the low index (or coupling) layer thickness. The second "mirror" of the cavity is the upper high index/low index boundary where total internal reflection occurs. This boundary is therefore 100% reflecting.

As with a Fabry-Perot cavity, resonance only occurs when the round trip phase delay between the mirrors is equal to a multiple of $2\pi$ radians. At resonance, the intensity of light in the cavity is high, at other times it is virtually zero. As the cavity has one totally reflecting boundary, all light is reflected from the resonant mirror device, both on and off resonance. However, the phase of the reflected light undergoes an additional change of $\pi$ radians on resonance. It is the phase of the reflected light which is monitored in the resonance mirror device.

The incident angle at which resonance occurs is such that the total round trip phase delay, which consists of the distance travelled between the two boundaries of the high index layer together with the phase change on reflection at each boundary, is equivalent to a whole number of wavelengths. Any binding reaction occuring at the top surface changes the phase change on reflection at the upper boundary. To achieve resonance the incident angle must be changed to compensate for this.

In a low loss system, the range of angles over which the resonant phase change occurs is very narrow and so very small changes in the resonant angle corresponding to small surface changes, can be detected.

The object of this invention is to enable the phase change on resonance occuring in an optical evanescent wave sensor device having a dielectric cavity to be observed more easily.

According to the invention there is provided an optical sensor comprising means for producing a beam of light with coherent TE and TM components, an optical evanescent wave sensor device having a dielectric cavity and arrange in the path of said beam of light for coupling said beam of light thereto, and an angular arranged to receive said components of the beam of light reflected from the device for producing a bright band and/or dark band, when one of said components excites resonance in said device.

Further according to the invention there is provided a method of testing a biochemicl sample, comprising providing an optical evanescent wave sensor device having a dielectric cavity and a sensing layer which is in at least in part sensitized by said sample, coupling a beam of light with coherent TE and TM components to said device to excite resonance in said device, and projecting said components of beam of light reflected from said device onto an analyser for producing a bright band and/or dark band.

By TE component is meant a component whose electric vector is perpendicular to the plane of incidence of the beam of light and by TM component is meant a component whose electric vector is in the plane of incidence of the beam of light.

The resonant mirror device which may be used in the optical sensor embodying the invention is simple in construction, consisting of a prism structure onto which one low and one high index dielectic film is deposited. These form a resonant cavity on the totally internally reflecting face of the prism. Antibodies for the species to be detected are immobilized onto this surface. Light is reflected off this surface within the prism and the phase of the reflected light is monitored. As the detected species binds to the antibody layer the angle at which resonance occurs changes, and this can be detected as a measure of the concentration of the detected species in the test sample. When the device is illuminated by a collimated polychromatic beam at an appropriate angle, only one wavelength will be on resonance. The wavelength at which resonance is excited may be monitored for testing the biochemical sample. This would require in the output optics means for wavelength demultiplexing, such as a diffraction grating or high dispersions prism. When the device is illuminated with a collimated beam from the tunable source, a resonance will occur at one particular wavelength. This wavelength can be monitored for testing the sample.

The device may be arranged in the path of the beam of light such that the resonance is excited for both of said components.

Preferably the input optic for the beam of light includes a lens arranged in the path of said beam of polarized light for focusing the beam of light onto the device, thereby providing simultaneously a range of angles of incidence at which said beam of light is coupled into said device.

Preferably the beam of light is linearly polarized with TE and TM components by a polarizer arranged in the path of the beam of light.

The polarizer may be arranged at 45° to the TE and TM transmission axes for providing equal components of TE and TM light and the analyser may be arranged at 90° to the polarizer for providing said bright band on to the viewing plane.

The sensor device may be a grating structure such as disclosed in PCT/GB89/01461, which includes a dielectric resonance cavity and an optical grating provided at one of the principal plane faces of the dielectric cavity for coupling light into the cavity.

Alternatively the device may be a resonant mirror device arranged in combination with coupling means for coupling light into said device. One example of such device and coupling means is disclosed in GB 2174802B.

Preferably said coupling means is a prism or diffraction grating mounted, together with said device, on a rotatable platform. The prism or diffraction grating together with said device may be mounted on a manually operable Vernier rotor stage so that angles of resonance can be measured. Preferably said resonant mirror device is fabricated on a surface of the prism or diffraction grating.

The output optics for the reflected light may include a compensator disposed adjacent said analyser to remove any phase difference which is introduced between the TE and TM components on total internal reflection and by birefringence in the device.

The bright band or dark band may be formed on a viewing plane at a position thereon corresponding to the angle of incidence at which resonance is excited in said device. The sensor may further include a CCD array connected to CRO for displaying said bright band or dark band on the screen thereof.

The beam of linearly polarized light with TE and TM components may be produced by a laser and a half wave plate disposed in the path of a beam of light produced by said laser.

The invention will now be described further by way of example with reference to the accompanying drawing in which.

Figure 1:
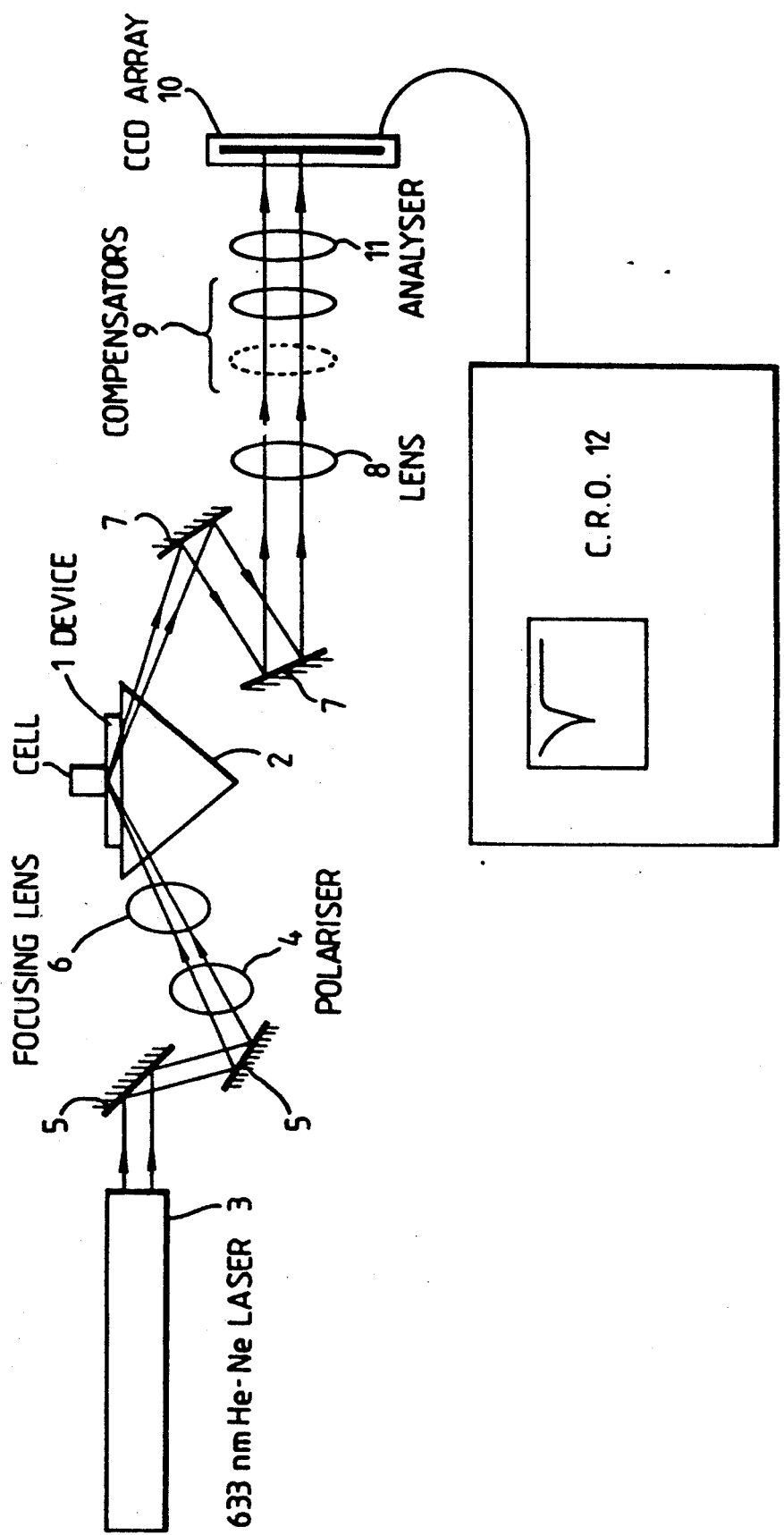
FIG. 1 illustrates an optical sensor according to the invention for use with a resonant mirror device.
Figure 2:
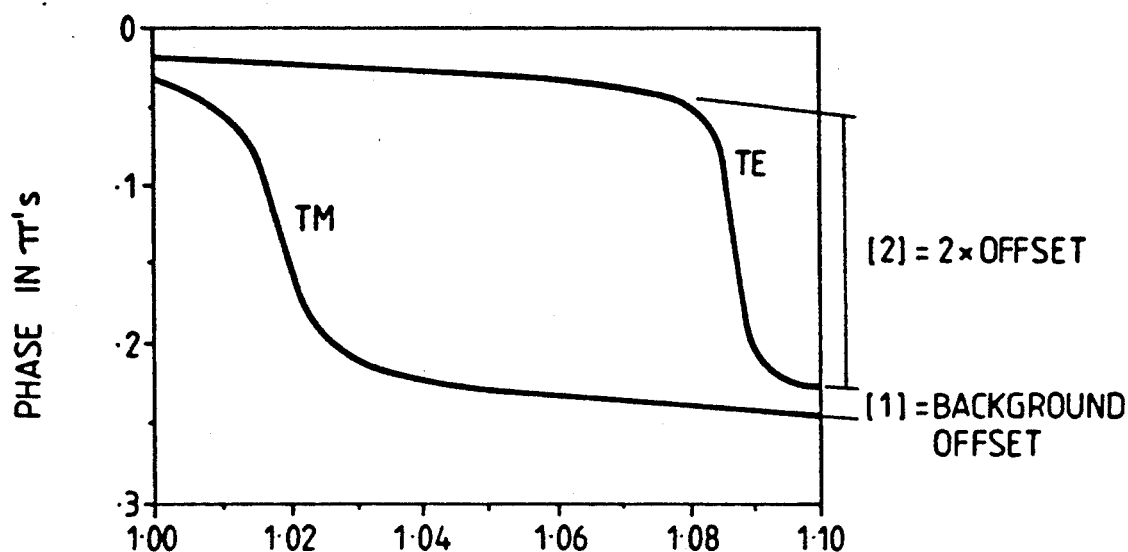
FIG. 2 is a graph of a phase shift on reflection versus angle for TE and TM reflected waves, note that the steps (2) associated with the resonances are both of $2\pi$ height, and that there is, or may be, a small offset (1) which is corrected by the compensator.
Figure 4:
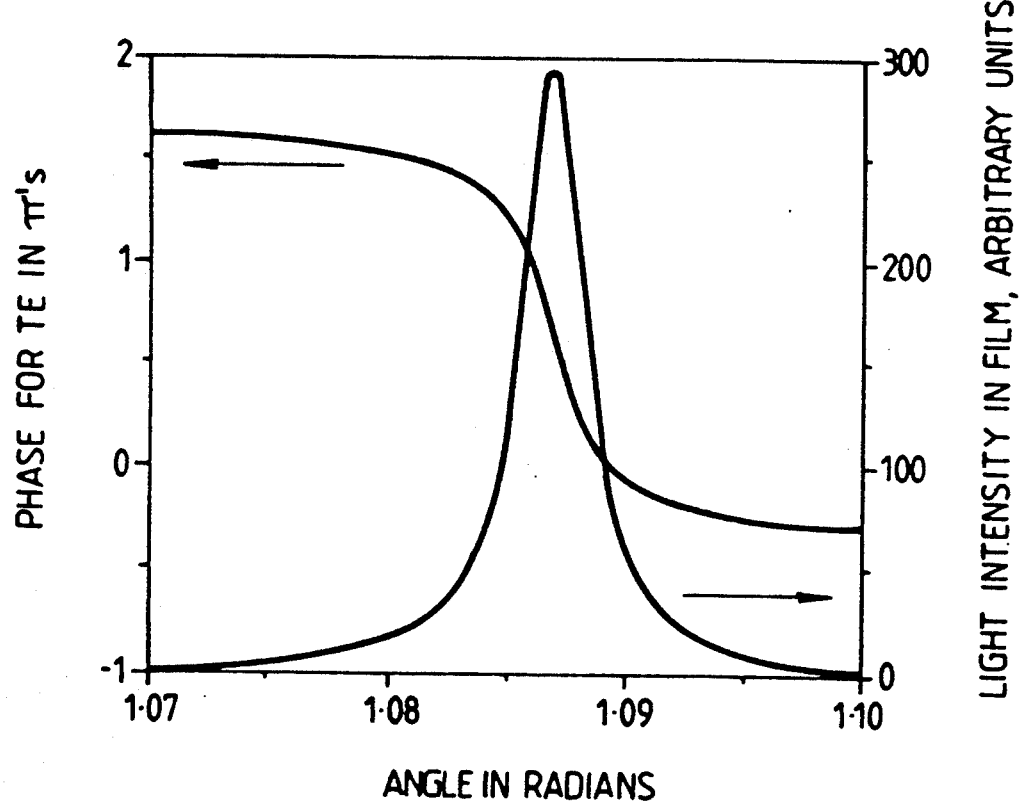

FIG. 4 is a double plot showing the phase v angle for TE component as in FIG. 2, and the corresponding light intensity in the sensed film. This shows that the width of the phase step and the width of the resonance are the same. Arrows indicate the relevant ordinate for each graph.

Referring to the drawings, the resonant mirror device and the coupling device disposed adjacent thereto are mounted on a rotatable platform. Preferably the platform is a manually operable Vernier rotor stage so that angles of resonance excited in the device can be measured. The coupling device is a prism 2 as shown in the drawing. The prism 2 couples light into the device at an angle of incidence depending on the angular position of the rotatable platform relative to the beam of light. A diffraction grating may be used instead of a prism for coupling light into the device.

The input optics, provides a wedge beam of light allowing a range of input angles of incidence to be monitored. The input beam of light is produced by a laser 3 such as He-Ne laser with a wave length of 633 nm. The beam of light from the laser 3 is passed on to a polarizer 4 through light reflectors 5. The polarizer is arranged to produce a linearly polarized light with two components transverse electric (TE) and transverse magnetic (TM). The polarizer is set at 45° to the TE and TM transmission axes and thus provides equal components of TE and TM light. Alternatively the polarized beam of light with TE and TM components may be produced by a polarized laser and a half wave plate. TE component undergoes a phase change on reflection which is different compared with TM component.

Figure 3:
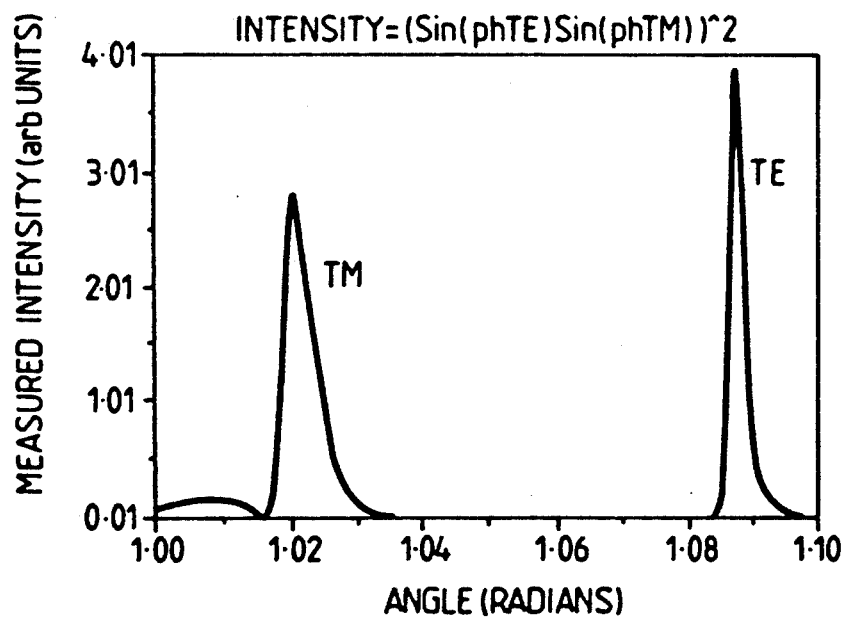
FIG. 3 is a graph of intensity signals for TE and TM components v angle derived for the above FIG. 2.

As with all SP and resonant mirror devices there is a resonance at some angle '0', at which a plane wave incident on the structure will produce a maximum intensity in the resonant film. This maximum will typically be many ($10^2+$) times the intensity produced at other angles of incidence. All the light is reflected for any angle of incidence, so the resonance is detected because of the effect on the phase of the reflected wave. See for example FIG. 2, showing the resonance and the resulting phase. Note that the width '$\Delta\phi$' is the same for both curves. Because the materials affect the electric component of the light wave differently from the magnetic component, the resonance occurs at different angles for the TE and TM input waves. Assuming the angular separation between TE and TM resonances is large compared with their angular width, as is normally the case, the phase of each component could be shown as in FIG. 2. The step height for either TE or TM as shown in FIG. 2 is $2\pi$. There may also be a 'background' phase difference between the curves at all angles 0 as shown in diagram 1 which is removed by the compensator. If this is done, remembering that a phase difference of $2\pi = 0$ (see FIG. 4), then a curve like FIG. 3 is obtained. This could also be described as $$\frac{1 - \text{Cos(Phase } TE - \text{Phase } TM)}{2}$$

The linearly polarized light produced by a polarizer 4 is focused by a lens 6 on the device 1. The beam of light focused on the device is in the form of a wedge beam as shown in the drawing thus allowing a range of angles to be scanned simultaneously. The platform on which the prism 2 is mounted can be rotated so that the angles of incidence at which both components are coupled into the device can be adjusted. The prism is rotated so that the beam coupled into the device strikes the device at angles of incidence at which a resonance is excited for at least one of the TE and TM components. The prism may be rotated to a position where the resonance is excited for both of said TE and TM components.

In a resonant mirror device including a substrate of Corning glass with refractive index of 1.639, a coupling layer of magnesium fluoride of refractive index 1.38, a layer of zirconium oxide of refractive index 2.05 and an aqueous overlayer of refractive index 1.33, the TE resonance occurs at an angle of 60° 44' with a resonance width of 4.2' and TM resonance occurs at 56° 58' with a resonance width of 24'. On to this structure a layer of refractive index 1.436 and thickness 60 A corresponding to a monolayer of the protein immunoglobulin C (Tg) is provided. This produces a change in the resonant angle of 9.0' for TE and 4.5' for TM. The angles of resonance may be measured by the pointer and scale provided on a Vernier rotor stage on which the prism 2 and the device 1 are mounted.

The reflected light from the device 1 is passed on to an analyser 11 through an output optics including reflectors 7, lens 8 and compensator 9. The analyser 11 is arranged at 90° to the polarizer. The two components are interfered at the analyser to allow the phase change on resonance to be detected. Off resonance both components undergo a similar phaseshift on total internal reflection and the relative phase between the components is adjusted by the compensator to give zero transmission through the analyser. This will apply for all angles except near resonance. Near resonance of either component, the phase shift between the TE and TM components will vary rapidly with angle, resulting in a maximum throughput of the analyser at resonance when all the light is transmitted. If a range of angle is scanned at once by using a wedge beam, a bright line on the dark background is projected onto the viewing plane. On rotating the analyser 90°, a dark band appears on a bright background on the viewing plane. A polarizing beamsplitter may be used to give both bright and dark band on the viewing plane. If the resonant angle changes, so does the position of the bright band and/or dark band on the viewing plane.

The lens 8 in the output optics is positioned at a focal length from the device and at a focal length from the viewing plane. This expands and collimates the beam whilst removing any diffraction effects. The compensator 9 consists of two quarter wave plates which are manually adjusted to remove any phase difference which is introduced between the TE and TM components on total internal reflection and by birefringence if the optical path.

The bright band of light from the analyser may be projected on a Charge Coupled Device array 10 (CCD array); the position of the bright band on the CCD array corresponds to the angle of resonance. Thus a shift of position of the bright band on the CCD array corresponds to a shift in the resonance angle. The output of CCD is passed on to a Cathode Ray Osciloscope 12 (CRO) for display on the screen. Calibrating the division across the CRO screen using the Vernier on which the prism is mounted allows the calculation of the angular width of the resonance.

I claim:

1. An optical sensor for testing a biochemical sample, the optical sensor comprising means for providing a beam of light, a polarizer arranged in the path of the beam of light to linearly polarize said beam of light with coherent TE and TM components, an optical evanescent wave sensor device arranged in the path of said polarized beam of light, said sensor device having a dielectric cavity and a sensing layer which is at least partly sensitized by said sample, the beam of light being polarized at approximately 45° at the surface of the cavity, coupling means for coupling said beam of light with coherent TE and TM components to said sensor device and an analyzer arranged to receive said components of the beam of light reflected from the device for producing at least one of a bright band and a dark band, when at least one of said components excites resonance in said device.

2. A sensor as claimed in claim 1, including a lens arranged in the path of said beam of light for focusing the beam of light onto the device, thereby providing simultaneously a range of angles of incidence at which said beam of light is coupled into said device.

3. A sensor as claimed in claim 1, in which said coupling means is one of a prism and a diffraction grating.

4. A sensor as claimed in claim 3, in which said device is fabricated on a surface of one of said prism and said diffraction grating.

5. A sensor as claimed in claim 4, in which one of said prism and said diffraction grating together with said device is mounted on a manually operable Vernier rotor stage so that angles of resonance can be measured.

6. A sensor as claimed in claim 1, including a compensator disposed adjacent said analyzer to remove any off resonance phase difference which is introduced between the TE and TM components.

7. A sensor as claimed in claim 1, including a CCD array for monitoring one of said bright band and said dark band.

8. A method of testing a biochemical sample, the method comprising providing a beam of light, linearly polarizing said beam of light with coherent TE and TM components, arranging in the path of said polarized beam of light, an optical evanescent wave sensor device having a dielectric cavity and a sensing layer which is at least partly sensitized by said sample, the beam of light being polarized at approximately 45° at the surface of the cavity, coupling said beam of light with coherent TE and TM components to said sensor device to excite resonance in said device for at least one of said components and arranging an analyzer to receive said components of the beam of light reflected from the device for producing at least one of a bright band and a dark band.

* * * * *